US00PP11439P

United States Patent [19]

Tamas

[11] Patent Number: Plant 11,439

[45] Date of Patent: Jul. 11, 2000

[54] BLACKCURRANT PLANT NAMED 'TITANIA'

[75] Inventor: Pal Tamas, Tollarp, Sweden

[73] Assignee: Dick McGinnis, Courtenay, Canada

[21] Appl. No.: 09/046,626

[22] Filed: Mar. 23, 1998

[51] Int. Cl.[7] ..... A01H 5/00

[52] U.S. Cl. ..... Plt./156

[58] Field of Search ..... Plt./156, 203

[56] References Cited

U.S. PATENT DOCUMENTS

P.P. 9,889 5/1997 Anderson ..... Plt./156

P.P. 9,975 7/1997 Anderson ..... Plt./156

OTHER PUBLICATIONS

9 Citations from UPOV–ROM GTITM computer database.

*Primary Examiner*—Howard J. Locker
*Assistant Examiner*—Wendy A Baker
*Attorney, Agent, or Firm*—Chernoff, Vilhauer, McClung & Stenzel

[57] ABSTRACT

A new variety of black currant plant from a planned cross is characterized by its large, firm berries which are able to withstand mechanical harvesting over an extended period and are well-suited for juice production, by its resistance to mildew and rust and by its upright vigorous growth.

3 Drawing Sheets

BACKGROUND AND SUMMARY OF THE INVENTION

This invention relates to a new and distinct variety of black currant (Ribes) which is the result of planned cross-breeding. The male parent is the $F_1$ hybrid of the cross: 'Consort'×'Kayaanin Musta'. The female parent is 'Altaskaya Dessertnaya'. These three varieties are not covered by U.S. patents or patent applications. The cross was made by Pal Tamas, a Swedish citizen, in Tollarp, Sweden in 1969, the plant was selected for further evaluation in 1974.

The following characteristics of the subject variety distinguish it from other black currants:

A. Extraordinary vitality, as expressed by the following:
   1. By the end of the first year, the subject variety is capable of forming a dense row of upright, tall (110 to 150 cm) basal shoots;
   2. The variety produces a crop of about two tons/hectare;
   3. The variety generally produces a full harvest in the third year, about one to two years earlier than the other known cultivars.

B. The variety possesses a high degree of autocompatibility which is the cause of the following:
   1. Berry size is uniform within a given cluster;
   2. Small or poorly developed berries (0.3 g or less) are virtually absent;
   3. Large and regular harvests can be obtained in monoculture without the necessity of co-cultivation of another variety as pollen donor.

C. The fruits of the variety are very large. Average berry size is between 1.1 and 1.3 g. The largest berries can reach 3.0 g.

D. The nutritional value of the fruit is very high as measured by its content of organic acids, ascorbic acid, pigments and total dry matter. Each of these variables exceed the average values obtained from a survey of an international list of black currant cultivars. *Berryfruit Varieties At Reduced Plant Protection*, BCV Expo. State School and Experimental Station for Viticulture and Orcharding, Weinsberg. The pigments of the fruits show great resistance against oxidative discoloration (i.e., browning). For this reason, the variety is regarded as a high quality source material for fruit juice production.

E. The berries are extremely attractive as frozen fruit.

F. The variety is resistant to mildew and black currant rust.

The new variety has been reproduced asexually by hardwood and softwood cuttings at Tollarp and Friseboda, Sweden. All subsequent asexually reproduced plants have been true to form in all respects, through multiple generations.

Figure 1:
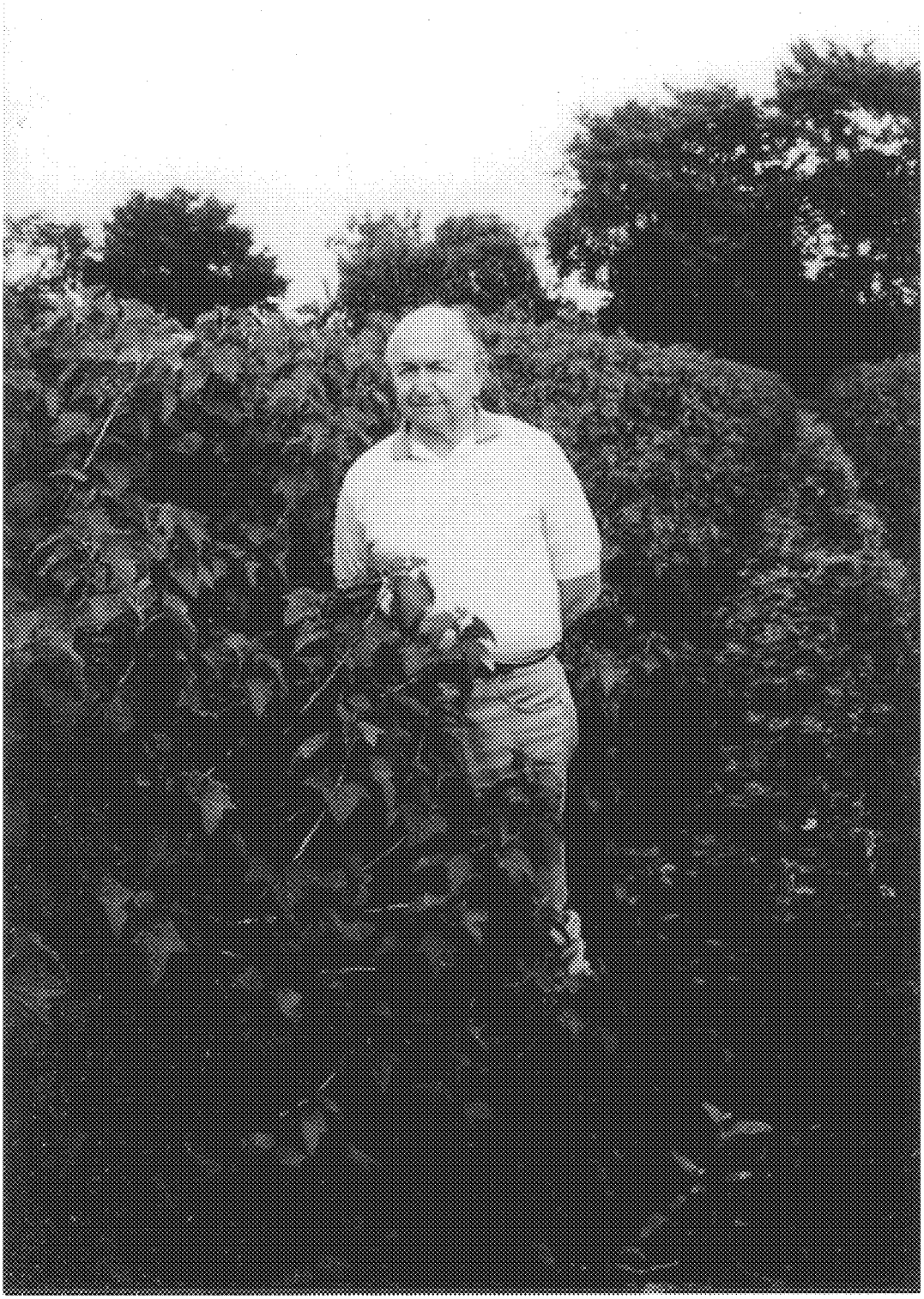
FIG. 1 shows a field of well-developed plants.
Figure 2:
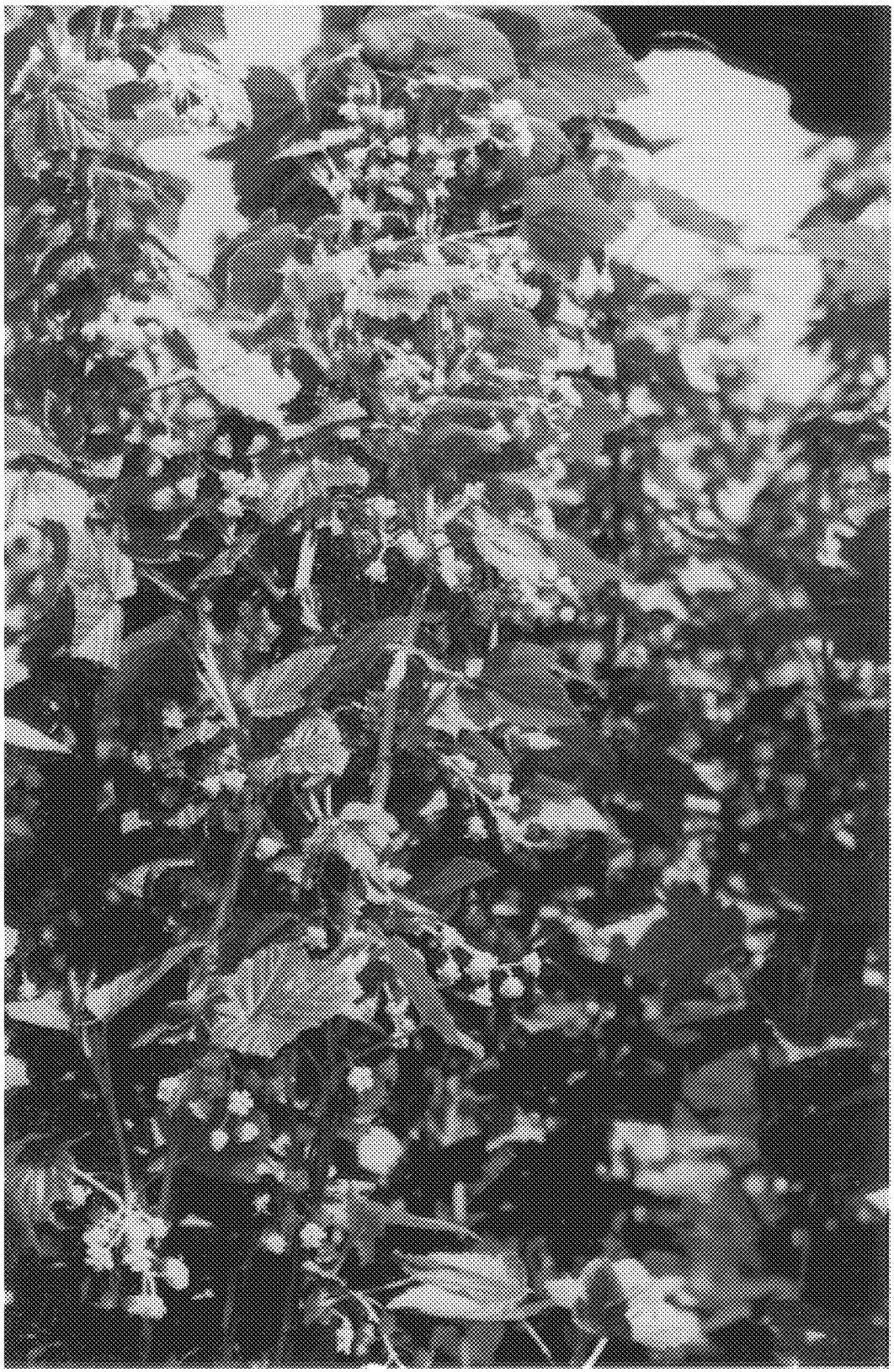
FIG. 2 shows a truss with the plant in bloom.
Figure 3:
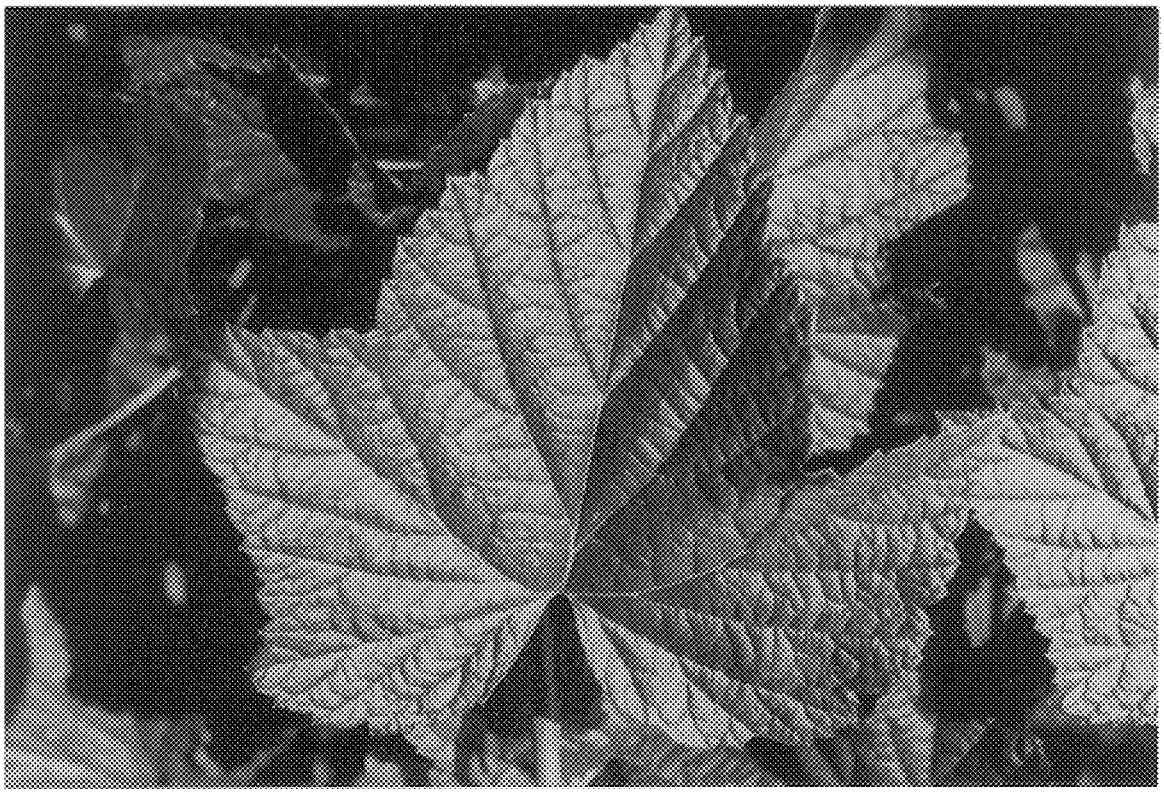
FIG. 3 shows a leaf.
Figure 4:
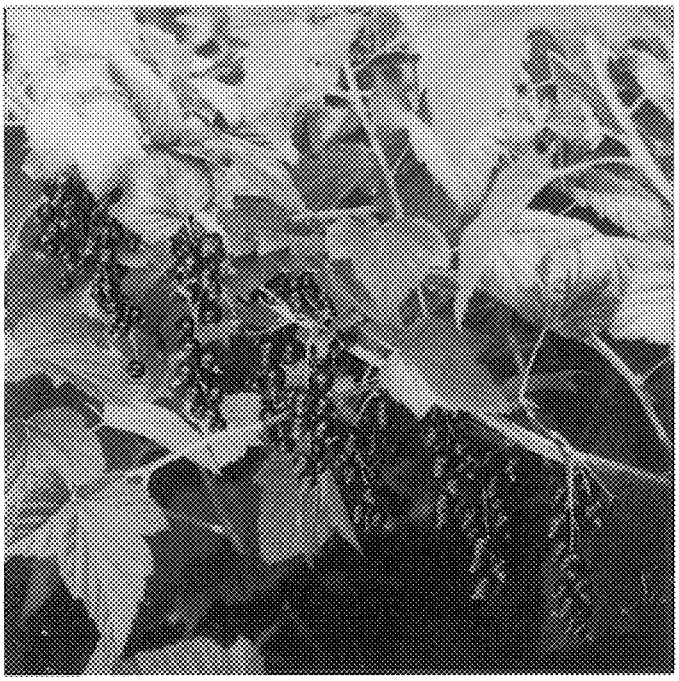
FIG. 4 shows the fruit on a plant.

Following is a detailed description of the new variety. The description is based on plants grown at Bundessortenamt in the Federal Republic of Germany in 1979 and on subsequent observations of plants grown in Sweden, Hungary, Germany and Finland. The variety has not been grown in the United States. Color references are to the Munsell Book of Color.

DETAILED DESCRIPTION OF THE CULTIVAR

Plant:

*Growth habit.*—Upright branches are spreading due to high fruit weight; thus the growth habit is high-round.

*Size.*—Well-developed plants are generally 160 to 220 cm high depending on location and cultivation.

*Shape.*—High, round.

*Basal shoots.*—Very few can be found in mature stands, but pruning can induce 25–40 basal shoots per plant.

*Intensity of growth.*—Unusually strong.

Leaf:

*Shape.*—Lobed.

*Tip.*—Acuminate.

*Margin.*—Serrate.

*Length.*—14.0 cm, 18.6 cm with petiole.

*Width.*—14.9 cm.

*Cross section.*—Straight (flat).

*Middle leaflet.*—Curvature is absent; the ratio of length to width is about 1 to 1.

*Upper surface.*—Main color: Dark green 7.5GY: 5/2. Tint: Bluish 5BG: 7/8. Gloss: Minimal. Blistering: Average.
*Under surface.*—Main color: Green 7.5GY: 6/4.
*Base.*—Cordate, slightly open.
*Petiole.*—Green with slight anthocyanin coloration near the base.
*Cross-section.*—Even.
*Curvature of middle lobe.*—Present.
*Length of middle lobe.*—Short.

Inflorescence: Mainly 1–2 bunches per bud.

Sepal:
*Color.*—Yellow green 2.5GY: 8/10.
*Anthocyanin coloring.*—Exists.
*Strength.*—Average.
*Shade.*—Reddish purple 2.5RP: 4/12.

Bud:
*Morphology.*—Elongated oval.
*Color.*—Red 5R: 6/10.
*Number of flowers per truss.*—7.9 (average 1992–1998 Poloske, Hungary).
*Orientation.*—Forms a wide angle with the stem.
*Size.*—Medium.
*Anthocyanin color.*—Strong during winter, otherwise average.
*Hairs.*—Medium density.
*Bud scales.*—Tip rounded.
*One-year shoots.*—Shape of the stigma at the first of the leaf stalk — very flat, triangular.
*Young growth.*—Anthocyanin coloring reduced.
*Strength.*—Little.
*Pubescence.*—Average.

Calyx:
*Color.*—Yellowish green to olive green 2.5Y: 6/6.
*Anthocyanin color.*—Occasional. Intensity: Slight to medium. Tint: Reddish-purple 2.5RP: 4/12.

Truss:
*Length.*—39 mm.
*Length of base.*—4.8 mm.
*Size.*—Generally long.
*Appearance.*—Loose.
*Frequency.*—Generally one or two per bud.

Fruit:
*Size.*—Very large, generally 1.1 to 1.35 g.
*Number of berries per truss.*—1992 — 8.1, 1993 — 5.5, 1994 — 6.1, 1995 — 7.3, average — 6.8 (Poloske, Hungary).
*Shape.*—Flattened sphere.
*Firmness.*—Very high.
*Color.*—Black, glossy 10RP: 2/1, lacks wax.
*Taste.*—Sweet, slightly acidic.
*Ripening.*—Medium-late (relative to "Triton": is about 10 days later in Southern Sweden, about 5 to 6 days later, about May 7 to Jun. 14, in Poloske, Hungary).
*Acid content.*—44.0 to 46.5 g/L. Ascorbic acid: 100 to 120 mg/100 g. Weight of 100 berries: High.
*Budding time.* —Average. Bud burst: March 14 (average 1992–1995 Poloske, Hungary). Bloom time: April 6–May 7 (average 1992–1995 Poloske, Hungary).
*Seed color.*—10R: 3/4.

Disease resistance: Resistant to mildew (*Sphaerotheca mors-uvae*) and to black currant rust (*Cronartium ribicola*); sensitive to *Drepanopeziza ribis.*

I claim:

1. A new variety of black currant plant substantially as shown and described herein, characterized by its unusually high growth and vigor and upright shape, uniformity of berry size, firm fruit which allows harvest over an extended period, its resistance to mildew and rust and the quality of its fruit which is well-suited for the production of juices and concentrates and for frozen fruit.

* * * * *